(12) United States Patent
Myer et al.

(10) Patent No.: US 11,337,291 B2
(45) Date of Patent: May 17, 2022

(54) SMART LIGHT BULB WITH SWITCH CONTROL

(71) Applicants: Aaron L Myer, Kanarraville, UT (US); Seth Myer, Eagle Mountain, UT (US)

(72) Inventors: Aaron L Myer, Kanarraville, UT (US); Seth Myer, Eagle Mountain, UT (US)

( * ) Notice: Subject to any disclaimer, the term of this patent is extended or adjusted under 35 U.S.C. 154(b) by 0 days.

(21) Appl. No.: 17/074,624

(22) Filed: Oct. 19, 2020

(65) Prior Publication Data

US 2021/0120654 A1 Apr. 22, 2021

Related U.S. Application Data

(60) Provisional application No. 62/923,382, filed on Oct. 18, 2019.

(51) Int. Cl.
| | | |
|---|---|---|
| *H05B 47/19* | (2020.01) | |
| *H05B 47/165* | (2020.01) | |
| *H05B 47/115* | (2020.01) | |
| *H05B 45/22* | (2020.01) | |
| *H05B 45/325* | (2020.01) | |
| *H05B 45/12* | (2020.01) | |
| *A61M 21/02* | (2006.01) | |
| *A61M 21/00* | (2006.01) | |

(52) U.S. Cl.
CPC ............. *H05B 47/19* (2020.01); *A61M 21/02* (2013.01); *H05B 45/12* (2020.01); *H05B 45/22* (2020.01); *H05B 45/325* (2020.01); *H05B 47/115* (2020.01); *H05B 47/165* (2020.01); *A61M 2021/0044* (2013.01); *A61M 2205/3303* (2013.01); *A61M 2205/3592* (2013.01); *A61M 2205/505* (2013.01); *A61M 2205/52* (2013.01); *A61M 2230/005* (2013.01)

(58) Field of Classification Search
CPC ...... H05B 47/19; H05B 45/20; H05B 39/088; H05B 47/105; H05B 47/115; H05B 1/0227; H05B 3/008; H05B 45/10; H05B 45/12; H05B 45/22; H05B 45/325; H05B 45/37; H05B 45/395; H05B 47/10; H05B 47/11; H05B 47/165; H05B 47/175; H05B 47/185

See application file for complete search history.

(56) References Cited

U.S. PATENT DOCUMENTS

| | | | |
|---|---|---|---|
| 2010/0029268 A1* | 2/2010 | Myer ................... | F21S 9/043 455/426.1 |
| 2018/0114434 A1* | 4/2018 | Newman, Jr. ......... | G05B 15/02 |
| 2021/0185789 A1* | 6/2021 | Smith .................... | H05B 47/19 |

* cited by examiner

*Primary Examiner* — Monica C King

(57) ABSTRACT

The invention is a smart light bulb device with a control system that is screwed into an existing light bulb socket. The smart light bulb device is powered via a light switch from a building's electrical system and is controlled by the control system that adjusts light output. The smart light bulb device also includes a processor, non-transitory memory for data storage, at least one input device, a network device, a wireless transmitter and receiver, and an antenna. In some embodiments, the input device is a motion sensor that turns on the light based on motion. In another embodiment, toggling the light switch on or off sends a signal to the controller to turn on or off the light or may also select a lighting scene based on the number of toggles. Individual smart bulbs and a network of multiple smart light bulb devices may be controlled by a mobile device.

20 Claims, 3 Drawing Sheets

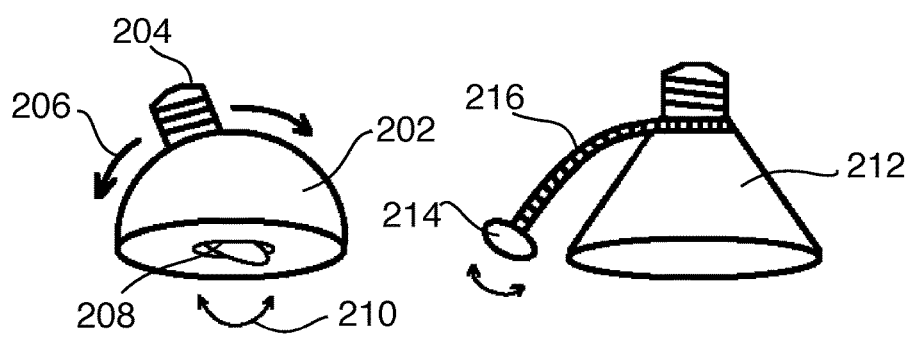
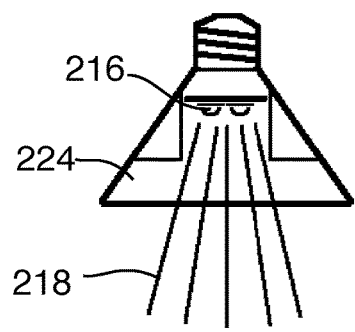
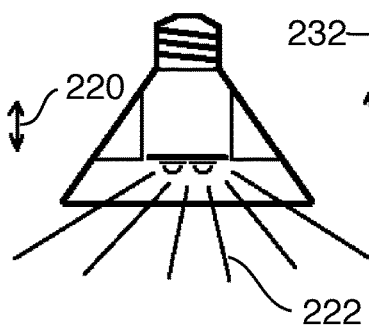
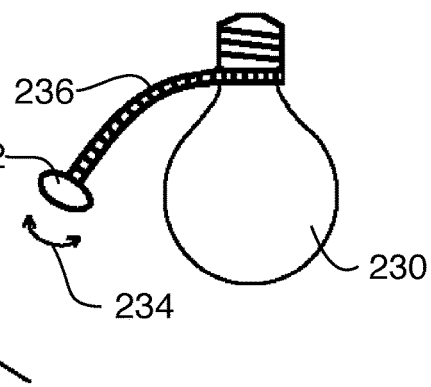
FIG. 2A   FIG. 2B
FIG 2C   FIG 2D   FIG. 2E

SMART LIGHT BULB WITH SWITCH CONTROL

RELATED APPLICATIONS

This patent application claims the benefit of U.S. Provisional Patent Application No. 62/923,382, filed Oct. 18, 2019, which is hereby incorporated by reference in its entirety.

TECHNICAL FIELD

This invention relates to automated lighting systems that do not require an electrician for installation.

BACKGROUND

Most modern lighting systems require a licensed electrician to replace the light switches in a home. In many cases the cost of installation of these systems exceeds the cost of the switches. This makes the cost of these types of systems out of reach for many people. Existing light-bulb centric systems are generally difficult to program, require an app or external systems to actuate, and fail completely when the existing light switches are used.

Therefore, a wirelessly controlled light bulb that incorporates a motion sensor, light sensor and wireless communications is needed. Other desired features include smart light bulbs in a home or business that are networked together and illuminate automatically in response to motion, and wherein the lighting needs and the habits of the occupants based on activity are sensed by the system to predict operation. A simple system that doesn't require an electrician for installation, changing out light switches or programming would also be desirable.

SUMMARY

In one aspect, the invention is a smart light bulb device with a control system that is screwed into an existing light bulb socket. The smart light bulb device is powered via a light switch from a building's electrical system and is controlled by the control system that adjusts light output. The smart light bulb device also includes a processor, non-transitory memory for data storage, at least one input device, a network device, a wireless transmitter and receiver, and an antenna. In some embodiments, the input device is a motion sensor that turns on the light based on motion. In another embodiment, toggling the light switch on or off sends a signal to the controller to turn on or off the light or may also select a lighting scene based on the number of toggles. Individual smart bulbs and a network of multiple smart light bulb devices may be controlled by a mobile device.

In a preferred embodiment, the smart light bulb device with a control system is screwed into an existing light bulb socket. The smart light bulb device is powered via a light switch from a building's electrical system and is controlled by the control system that adjusts light output. The smart light bulb device also includes a processor, non-transitory memory for data storage, at least one input device, a network device, a wireless transmitter and receiver, and an antenna. In some embodiments, the input device is a motion sensor that turns on the light based on motion. In another embodiment, toggling the light switch on or off sends a signal to the controller to turn on or off the light or may also select a lighting scene based on the number of toggles. Individual smart bulbs and a network of multiple smart light bulb devices may be controlled by a mobile device.

This invention has been developed in response to the present state of the art and, in particular, in response to the problems and needs in the art that have not yet been fully solved by currently available systems and methods. Features and advantages of different embodiments of the invention will become more fully apparent from the following description and appended claims or may be learned by practice of the invention as set forth hereinafter.

Consistent with the foregoing, a smart light bulb device is disclosed. The objectives of the system are to provide a smart light bulb device with a control system that is screwed into an existing light bulb socket. The smart light bulb device is powered via a light switch from a building's electrical system and is controlled by the control system that adjusts light output. The smart light bulb device also includes a processor, non-transitory memory for data storage, at least one input device, a network device, a wireless transmitter and receiver, and an antenna. In some embodiments, the input device is a motion sensor that turns on the light based on motion. In another embodiment, toggling the light switch on or off sends a signal to the controller to turn on or off the light or may also select a lighting scene based on the number of toggles. Individual smart bulbs and a network of multiple smart light bulb devices may be controlled by a mobile device.

In a preferred embodiment, a smart light bulb device may include at least one light source and a control system. The control system may adjust a light output of the light source. The light bulb device may also include a processor, non-transitory memory for data storage, stored settings in the non-transitory memory, at least one input device, a network device, a wireless transmitter, a wireless receiver, an antenna, and a light switch. The light switch may be an existing light switch installed in an existing building with existing electrical wiring connecting to an electrical power system in the building. This existing circuit may provide power to the smart light bulb device. The light switch may be one of the input devices. Switching the light switch on or off may send a signal to the processor. The control system may notify a user of the switch position. One or more toggling of the light switch position may send a different signal to the processor based on the number of toggles.

In another embodiment, the input devices may include one or more of a touch screen, a button, a dial, a motion sensor, a microphone, a proximity sensor, a pressure sensor, a motion sensor, a user interface device, a mechanical sensor, a vision sensor, an imaging sensor, a camera, a temperature sensor, a radiation sensor, a position sensor, a photoelectric sensor, a particle sensor, a humidity sensor, a gas or chemical sensor, a force sensor, a flow sensor, a voltage sensor, a current sensor, a contact sensor, a mechanical device, and an electrical sensor.

In one embodiment, the user interface device may include at least one of: a smart phone, a computer, an input device integrated to the lighting device, and a mobile device.

In an embodiment, the light switch toggle may inform the processor of a predefined lighting scene based on a number of toggles. In an embodiment, the network device may connect to an additional one or more network device in another one or more smart light bulb device. The network device may be connected to at least one of: a local area network, a wide area network and a cloud-based network.

In certain embodiments, the processor may send a control signal to the controller based on at least one of: one or more user inputs, a signal from the network device, and the stored settings. A system of networked smart light bulb devices may communicate that they are connected to the same light switch control by input from the user. The input from the user may be via the light switch toggle. In an alternate embodiment, the input from the user may be via a user input device.

In other embodiments, all of the smart light bulb devices in the system of networked smart light bulb devices may be controlled according to the stored settings and command signals transmitted via the network device. The system of networked smart light bulb devices may track all system inputs via sensors and other input devices to determine habits of one or more users. The system may build a profile for each user based on their habits and stores that profile in the memory. A model may be built representing the history of a user's profile over a time period; wherein the model is modified based on changes to the user's profile over the time period; wherein the model is stored in the stored settings.

In an embodiment, the invention may include an energy storage device. The energy storage device comprises at least one of: a capacitor and a battery. In other embodiments, the input device may receive a signal from the user's phone Bluetooth radio as an input. The input device may use the signal strength or Received Signal Strength Indicator to turn the smart light bulb device on when the user is close enough to the smart light bulb device. The input device may use the signal strength or Received Signal Strength Indicator to notify the control system that the user is close to the smart light bulb device. The control system may perform a predefined function based on a preprogrammed set of instructions based on the user's proximity to the smart light bulb device.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

FIG. 2A is a smart light bulb device with adjustable motion sensor.

FIG. 2B is a smart light bulb device with adjustable motion sensor.

FIG. 2C is a smart light bulb device with adjustable motion sensor.

FIG. 2D is a smart light bulb device with adjustable motion sensor.

FIG. 2E is a smart light bulb device with adjustable motion sensor.

DETAILED DESCRIPTION

Figure 1:
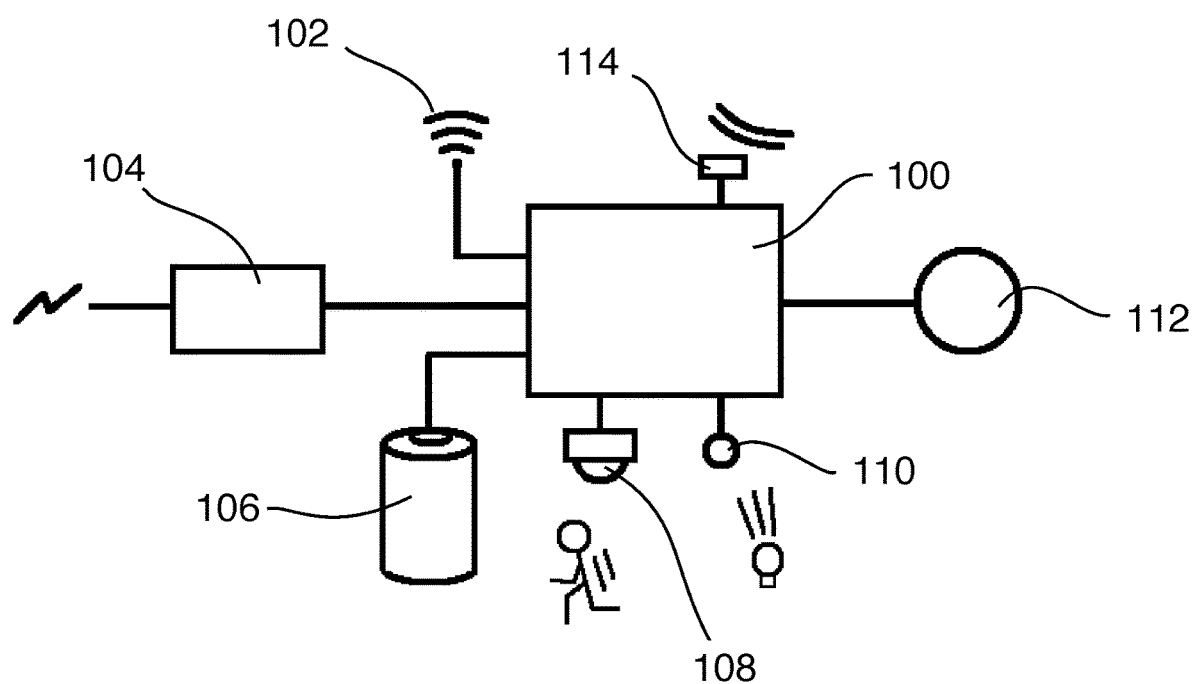
FIG. 1 is a diagram of the controller with attached components.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the terms "light", "light bulb" "auto light" or "bulb" all refer to the smart light bulb device. The term "system" refers to the system comprising one or more smart light bulb devices along with the control system that controls the one or more smart light bulb devices.

As used herein, every reference to a "light switch" is referring to an existing light switch in an existing building.

As used herein, every reference to a "lighting System" is referring to a group of networked smart light bulb devices.

FIG. 1 is a diagram of the controller with attached components. Controller 100 has attached components as follows: Antenna 102, Electrical high voltage 120 VAC input power supply 104, Battery 106, motion sensor 108, ambient light sensor 110, light output 112, and pressure sensor 114.

FIG. 2A is a smart light bulb device with adjustable motion sensor. This embodiment shows a lamp 202 with screw in component 204, adjustable base 206, and adjustable motion sensor 210

FIG. 2B is a smart light bulb device with adjustable motion sensor. This embodiment shows a lamp 212, with adjustable arm 216, and adjustable motion sensor 214.

FIG. 2C is a smart light bulb device with adjustable motion sensor. This embodiment shows a lamp 224 with sliding 220 motion sensor base 216 producing a narrow beam width 218.

FIG. 2D is a smart light bulb device with adjustable motion sensor. This embodiment shows a lamp with sliding 220 motion sensor base producing a wide beam width 222.

FIG. 2E is a smart light bulb device with adjustable motion sensor.

Figure 3:
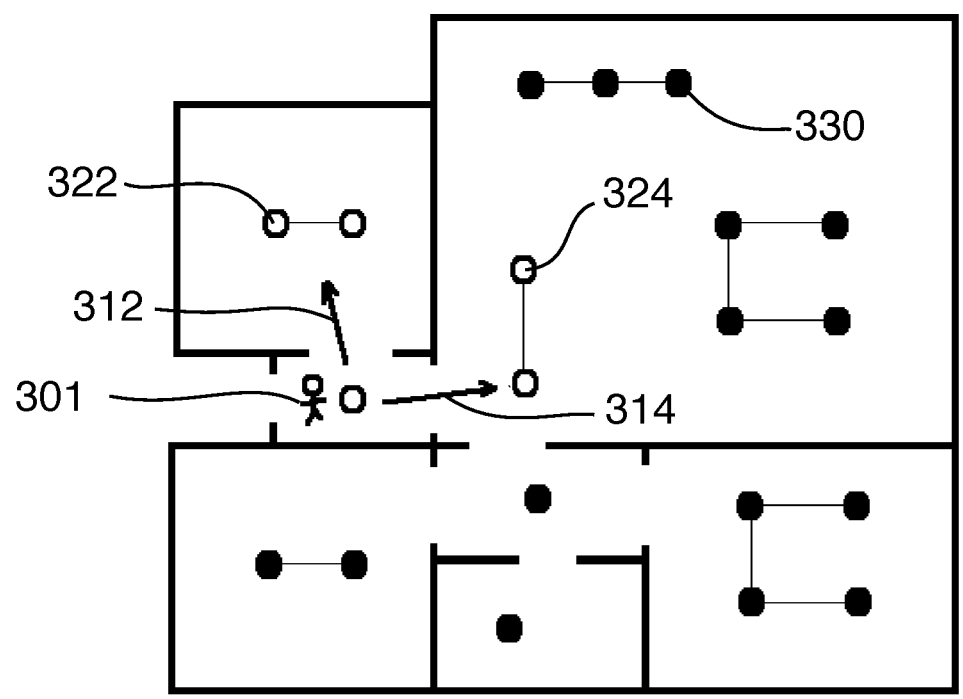
FIG. 3 is a diagram of a user moving through a floorplan space.

FIG. 3 is a diagram of a user moving through a floorplan space.

The auto light is a wirelessly controlled light bulb that incorporates a motion sensor, light sensor and wireless communications. Multiple auto lights in a home or business illuminate automatically in response to motion, lighting needs and the habits of the occupants based on activity.

The most interesting part of this lighting system is the simplicity. It doesn't require an electrician for installation, is as easy as changing a light bulb. The system doesn't need to be programmed, because it adapts to operate based on the habits of the occupants.

DETAILED DESCRIPTION

Installation and Setup

A user may replace the light bulbs in his home with auto-light bulbs, and then switch the light switches to the ON position. When the bulbs receive power, they may communicate over the wireless network with other auto-lights. Each auto-light may compare their own power-up times with the other auto-lights found on the network and may use the power-up time information to determine which bulbs are connected to the same light switch. Turning on the light switch for the first time after replacing bulbs may complete the initial installation process, since all the bulbs on the same circuit may now be aware of the grouping.

Bulb May Respond to Motion with Built in Detector

Each light bulb may incorporate a motion sensor to detect occupancy and turn on automatically. The bulb may turn off automatically after a period of inactivity. The bulb may comprise a processor, non-volatile memory, a wireless radio, a motion detector and an ambient light sensor. Independent settings like turn on time, brightness and groupings may be stored in nonvolatile memory so the experience may be customized.

Bulbs May Synchronize Over Wireless Communications

Multiple bulbs may operate together by communicating events over the wireless link. For example, 3 bulbs in a hallway may be configured to turn on when any of the three detect motion. The wireless network may be Bluetooth Low Energy, Bluetooth mesh, ZigBee, 802.15.4, Wi-Fi or a proprietary network.

Bulbs May Auto-Detect Common Circuits

For ease of configuration, the bulbs may automatically detect when they are powered by a common switch. When the bulbs are installed and the light switch is turned on for the first time, the bulbs may wirelessly communicate the amount of time elapsed since the power was restored (boot time). Each bulb may compare their own boot time with other bulbs and may store information about which other bulbs booted at about the same time. All the bulbs on the same circuit may be associated with the same group and may respond together when any of the other bulbs in the group detect motion or receive other commands like on, off or dim to level. Once the auto light determines the other bulbs on a common circuit, it may save the information about the group in non-volatile memory so that it may retain the configuration and all bulbs may work together.

Light Toggle from Manual Switch Action

Since the new bulbs may respond to motion, the existing wall switch may be left on and is rarely needed. However, if the switch is turned off and immediately back on, the light may toggle state from off to on, or from on to off. The processor in the bulb may have sufficient reserve power using a battery or large capacitor so that it can detect an interruption of power as a button event and may react accordingly. The toggle from the manual switch function may allow these intelligent lights to be used manually, in almost the same way as a traditional light bulb.

Light Dim Level Set from Manual Switch Action

One embodiment of the bulb may include enough battery power to keep the light on during a power interruption. This may allow the wired wall switch to be used to adjust the dim level. If the switch is turned off and not immediately turned back on, the light may dim up (if it is off) or down (if it is on). When the wall switch is turned back on, the bulb may remain at the current dim level. Wall switch actions for dimming and toggling lights may also be communicated to the master controller to establish desired operation for "habit programming" described below.

Special Manual Functions

Toggling the manual switch on and off multiple times may trigger a scene or any other special function. For example, the switch by the front door may be configured to activate an "away" scene when it is toggled off and on twice in less than two seconds. The away mode may turn off some lights or turn the porch light on and keep it on, or may initiate random light changes to simulate an occupied home. Each circuit in the home may be configured with a different action so that many functions including scenes, groups and modes may be accessed with the existing wiring infrastructure.

Feedback and Two-Way Communication

The user may communicate with the bulb using motion or the manual switch (or a smart phone application). The bulb may communicate back to the user by flashing the light, or using and audible bell, buzzer, tone or voice feedback. For example, the bulb may chirp when the switch is left off for more than 5 seconds, indicating it was either turned off by accident or the power is out. Another example is after toggling the manual switch off and back on twice to active vacation mode, the bulb may announce "Vacation", chime or flash to acknowledge vacation mode has been activated.

Power Outage

The system may detect a system wide power outage (by comparing group power event timing) and may use the battery power for emergency lighting. Since the bulbs have intelligence and wireless communication, they may continue to operate in power outage mode and may adjust lighting behavior for maximum power saving. Depending on the battery capacity, each bulb may be able to light for several hours in power outage mode. In power outage mode, the bulbs may dim to reduce power usage, and shorten the on time based on motion detection, and may take other measures based on the configuration set by the app.

Power Shift

Many power companies charge more for power during peak hours than they do during off-peak hours. The auto-light bulb may be configured to charge the battery only at night, shifting power usage from peak hours to off-peak hours, saving money. When used in a solar powered home, the lights may charge when the sun is shining and may run off the batteries at night when no solar is being generated.

Power Saver Mode

Bulbs with battery power may track the maximum charge achieved during the day and may use the average daily usage to adjust the aggressiveness of power savings to maximize power savings. For example, a bulb that only charges to 50% during the day and is used at night may reduce the power output to 50% and shorten the on time to save power. When the battery is very low, the bulb may keep the light off and maintain motion sensing and communications to trigger nearby lights to turn on if they have power.

Solar Bulb

A solar version of the bulb may be used outdoors to charge when the sun is out and may be able to function without requiring grid power. The solar bulb may use the solar panel to detect ambient light, without needing an additional ambient light sensor.

Remote Control and System-Wide Control

System actions like house off, goodnight scene and vacation mode and remote access may all be possible when the bulbs communicate with each other or with a master controller or a cloud service over a wireless to IP bridge. A cloud service may allow control from Amazon Alexa, Google Home or other similar external systems. The cloud service may also allow remote access and monitoring from an app when there is a wireless to IP bridge device or a master controller that connects to both the lighting network and an IP or cellular network that has access to Internet services.

System Observes Habits of Occupants to Determine Desired Operation

The simple act of entering a room or turning off a light may be a way of telling the system what you want it to do. Since the system may be able to track movement and on/off events and dim levels, it may be natural and easy to establish a routine that the system can remember. For example, if you enter the kitchen every morning at 6:30 am and dim the lights up to 50%, the system may remember that and automatically turn the lights on to 50% when you enter the kitchen in the morning. If the lights in the living room turn on when you enter and you turn them back off, the system may disable motion detection in the living room. Or if you trigger the lights with motion in the pantry repeatedly because the lights went off too early, the system may adjust the on time in the pantry to keep the lights on long enough to provide a seamless experience.

The system may have access to motion, ambient light levels, time, sunrise and sunset and calendar, and the habits of people to establish a routine and operate accordingly without any programming or configuration. The concept of habit programming may apply to other devices in the home besides just the lights. Habit programming may be used to track thermostat programming, security system settings, opening and closing of blinds and shades, and automation of other tasks in the home like robot vacuuming, coffee pot scheduling, zone based heating and cooling and many other tasks.

The concept of habit programming may be implemented on a master controller that may be aware of all the devices in the system, or it may be implemented in a cloud service that may communicate with the bulbs over an IP to wireless bridge device.

It may also be possible to implement habit programming on the individual devices without any external master controller or bridge using information from other nodes in the system transmitted over the wireless network. Each node in the network may only need to track the habit-based triggers that affect itself (or its group), so each node may independently watch for patterns and store new patterns when they are accessed consistently. Each node may also remove bad habits when a habit-based event is triggered, and the user may cancel it by manually accessing the switch. For example, if I turn on the kitchen light at midnight for a snack 3 nights in a row, the kitchen light may remember that habit and automatically turn on the light at midnight on the fourth night. If I immediately turn off the light after that triggered event, the light may mark the habit as a bad habit and stop doing it. Habit programming may use artificial intelligence systems to learn the desired system behavior and configure or actuate the changes in the system.

Predictive Pathway Lighting

The system may track the pathway the occupants take through the home and may turn on the lights in the expected direction of travel. If the occupant takes a different path, the system may simply dim off the lights that weren't needed.

In this example, the user may enter the back door near light 1. Light 1 and 2 are in a group and both may turn on from motion detection. Past experience (from what the system has observed) may show that motion in the mudroom is usually followed by motion in the kitchen, so lights in group 3, 4, 5, 6 may turn on. From the kitchen the user may move toward light 7 (also determined by the system based on prior patterns), so the systems may turn on lights 7 and 8 because they are grouped. If no motion is detected by light 7 and 8, they may turn off after about 20 seconds. When the user passes light 6, lights 14, 13, and 10 may turn on in anticipation. When the user passes light 14 and enters the master bedroom, lights 13 and 10 may turn off, while 15-18 in the master bedroom group may turn on.

Ambient Light Pathway Prediction

Another method of lighting pathways may be by using ambient light detection. By sensing ambient light levels, a bulb may detect a nearby light turning on by the increase in ambient light. The bulb that detects the light increase may respond by turning on and may effectively light the pathways from the initial bulb with no other input required. For example, a person may walk into a room and the first light may detect the person with a motion sensor, then the first light may turn on.

Nearby lights may detect the change in ambient light from the first bulb turning on and may respond by turning on. A shorter time delay may be used when the bulb is triggered by ambient light, so that the lights don't stay on long unless the ambient light sensing is followed by motion sensing.

Ambient light sensing may also be used to turn off lights when nearby lights are turned off. By sensing the ambient light, on and off events may be synchronized between bulbs for a more pleasing experience.

The bulbs may also use ambient light levels to turn off to save energy when there is sufficient external lighting from windows, skylights or other fixtures Ambient Dark Sensing Another configuration option may use ambient light sensing to turn on the lights. For example, a person may manually turn off the bedroom light to go to sleep. The bedside lamps may detect the lights turning off and turn on to a dim level for a time to allow the person to walk to the bed without stepping on any legos or dogs.

Dim Level Adjusts Based on Time of Day and Ambient Light

The system may use the ambient light levels, time of day and sunrise/sunset to adjust the dim level of lighting in the home. For example, if movement is detected in the middle of the night, the lights may dim up to only 15% for safety but may remain low to make it easy to go back to sleep. Or if the lights have the ability to change color, they may stay dim red to make it easier for sleepy eyes to adjust. During mid-day hours the lights may turn on to 100% or may not turn on at all if there is sufficient ambient light.

App for Control and Advanced Settings

The smart phone application may allow access to scenes, advanced configuration, and remote access. Scenes may be room specific sets of lights and desired levels, or a scene may include the whole home—like a goodnight scene or a party scene. The app may also monitor energy use and report on usage, prediction success, and automation changes based on manual control events.

Vacation

Auto lights may be configured to simulate normal lighting activity while in vacation mode, turning on and off as if someone is home. Since the system may already be tracking movement, vacation mode may be realistic and effective with no programming—just by playing back events from an earlier day. For vacation mode the system may use the general trends established by the occupants and alter timing randomly to make the home appear to be occupied in vacation mode.

Security

Every light bulb may have a motion sensor, so the system becomes an effective home security monitor when the home is supposed to be unoccupied, or at night. By tracking movement inside the home in away mode, the system may easily detect a security breach and notify the owner via text message, email, or app notification. The motion detection may also inform security cameras of events and direction. The system may turn on all the lights when a breach is detected or may flash them to alert the neighbors of a problem.

Person Tracking

The lights may also use Bluetooth location services to track individuals using their cell phones and may adjust lighting preferences depending on who is home. This may also be used as part of the security feature to track ingress and egress.

Standalone Operation

The bulbs may communicate with each other directly over an ad hoc network that requires no setup (for example, Bluetooth, BT mesh, zigbee, z-wave or 802.15.4 wireless). The bulbs may be able to detect each other and configure themselves without user intervention, allowing complete functionality as a standalone system with absolutely no setup, no configuration and no provisioning required. This system may work as a standalone system by providing most of the benefits of an automated lighting system without any external connection. Even a phone app may not be required for setup. This may make the system an effective lighting solution that requires no setup, the hardest part of the installation may be screwing in a light bulb.

Scene Switch

An add-on switch may integrate with the bulbs to provide direct access to system scenes, modes and actions. This switch may be a Decora style switch that mounts in a standard gang box, or it may be a remote control or a switch that sticks on the wall or on top of the manual light switch. The scene switch may be battery operated and communicate with the bulbs over the wireless network. The switch may allow selection of scenes or groups, and may control dimming the lights, groups or scenes up and down.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

All patents and published patent applications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. A smart light bulb device comprising:
   at least one light source;
   a control system;
      wherein the control system adjusts a light output of the light source;
   a processor;
   non-transitory memory for data storage;
   stored settings in the non-transitory memory;
   at least one input device;
   a network device;
   a wireless transmitter;
   a wireless receiver;
   an antenna;
   a light switch;
      wherein an AC electrical system provides electrical power to the smart light bulb via the light switch;
   wherein the light switch is a manual switch which is one of the input devices;
   wherein switching the light switch on or off sends a signal to the processor;
   wherein the control system notifies a user of the switch position;
   wherein manually moving the switch position of the light switch from off to on supplies power to the smart light bulb;
   wherein manually moving the switch position of the light switch to the off position removes power from the smart light bulb;
   wherein manually moving the switch position of the light switch from off to on sends a first signal to the processor;
   wherein manually moving the switch position of the light switch from on to off sends a second signal to the processor;
   wherein one or more toggling of the light switch position from off to on, or from on to off sends a different signal to the processor based on the number of toggles.

2. The invention of claim 1, wherein the input devices comprise one or more of a touch screen, a button, a dial, a motion sensor, a microphone, a proximity sensor, a pressure sensor, a motion sensor, a user interface device, a mechanical sensor, a vision sensor, an imaging sensor, a camera, a temperature sensor, a radiation sensor, a position sensor, a photoelectric sensor, a particle sensor, a humidity sensor, a gas or chemical sensor, a force sensor, a flow sensor, a voltage sensor, a current sensor, a contact sensor, a mechanical device, and an electrical sensor.

3. The invention of claim 2, wherein the user interface device is at least one of: a smart phone, a computer, an input device integrated to the lighting device, and a mobile device.

4. The invention of claim 1, wherein the light switch toggle informs the processor of a predefined lighting scene based on a number of toggles.

5. The invention of claim 1, wherein the network device connects to an additional one or more network device in another one or more smart light bulb device.

6. The invention of claim 1, wherein the network device is connected to at least one of: a local area network, a wide area network and a cloud-based network.

7. The invention of claim 1, wherein the processor sends a control signal to the controller based on at least one of: one or more user inputs, a signal from the network device, and the stored settings.

8. The invention of claim 1, wherein a system of networked smart light bulb devices communicate that they are connected to the same light switch control by input from the user.

9. The invention of claim 8, wherein the input from the user is via the light switch toggle.

10. The invention of claim 8, wherein the input from the user is via a user input device.

11. The invention of claim 8, wherein the system of networked smart light bulb devices track all system inputs via sensors and other input devices to determine habits of one or more users.

12. The invention of claim 8, wherein all of the smart light bulb devices in the system of networked smart light bulb devices are controlled according to the stored settings and command signals transmitted via the network device.

13. The invention of claim 1, wherein the control system builds a profile for each user based on their habits and stores that profile in the memory.

14. The invention of claim 13, wherein a model is built representing the history of a user's profile over a time period wherein the model is modified based on changes to the user's profile over the time period; wherein the model is stored in the stored settings.

15. The invention of claim 1, further comprising an energy storage device.

16. The invention of claim 15, wherein the energy storage device comprises at least one of: a capacitor and a battery.

17. The invention of claim 1, wherein the input device receives a signal from the user's phone Bluetooth radio as an input.

18. The invention of claim 17, wherein the input device uses the signal strength or Received Signal Strength Indicator to turn the smart light bulb device on when the user is close enough to the smart light bulb device.

19. The invention of claim 17, wherein the input device uses the signal strength or Received Signal Strength Indicator to notify the control system that the user is close to the smart light bulb device.

20. The invention of claim 19, wherein the control system performs a pre-defined function based on a preprogrammed set of instructions based on the user's proximity to the smart light bulb device.

* * * * *